United States Patent [19]

Rabson et al.

[11] Patent Number: 5,244,635
[45] Date of Patent: Sep. 14, 1993

[54] CENTRIFUGE VESSEL WITH COAXIAL WASTE CHAMBER HAVING CAP TO PREVENT WASTE FLUID TRANSFER FROM THE CHAMBER INTO THE VESSEL

[75] Inventors: Arthur L. Rabson, Chester; Thomas Palmieri, Paramus, both of N.J.; Douglas R. Olson, Doylestown, Pa.

[73] Assignee: Cirrus Diagnostics, Inc., Chester, N.J.

[21] Appl. No.: 901,430

[22] Filed: Jun. 19, 1992

[51] Int. Cl.5 .................... G01N 33/544; C12M 1/16
[52] U.S. Cl. ................................ 422/72; 422/69; 422/71; 422/102; 494/16; 494/44; 436/524
[58] Field of Search ................ 494/16, 19, 38, 44; 422/69, 71, 72, 101, 102, 104; 436/524; 215/307, 310, 344, 345, 348, 356, 364; 220/523, 525

[56] References Cited

U.S. PATENT DOCUMENTS

| | | | |
|---|---|---|---|
| 1,956,496 | 4/1934 | Degerth | 494/44 X |
| 2,389,761 | 11/1945 | Burgeni | 215/348 |
| 2,768,762 | 10/1956 | Guinet | 215/345 X |
| 2,940,107 | 6/1960 | Sterling | 215/364 X |
| 3,125,547 | 3/1964 | Blatz | 525/199 |
| 3,219,728 | 11/1965 | Joris et al. | 525/198 X |
| 3,366,320 | 1/1968 | Cho | 215/344 X |
| 3,465,957 | 9/1969 | Brandt | 494/16 |
| 3,592,349 | 7/1971 | Baugh | 215/307 |
| 3,665,068 | 5/1972 | Duling et al. | 264/211 |
| 3,682,321 | 8/1972 | Smith | 422/101 X |
| 3,722,790 | 3/1973 | Natelson | 422/101 X |
| 3,760,969 | 9/1973 | Shimamoto et al. | 215/364 X |
| 3,773,468 | 11/1973 | Hubbard et al. | 422/102 |
| 3,849,256 | 11/1974 | Linden | 422/102 X |
| 3,918,912 | 11/1975 | Talonn | 422/47 |
| 3,985,032 | 10/1976 | Avakian | 422/101 X |
| 4,111,355 | 9/1978 | Ishimaru | 494/38 |
| 4,119,403 | 10/1978 | Rex | 422/83 X |
| 4,244,916 | 1/1981 | Guigan | 422/72 |
| 4,446,090 | 5/1984 | Lovgren et al. | 264/211 |
| 4,612,148 | 9/1986 | Motooka et al. | 264/211 X |
| 4,614,276 | 9/1986 | Ihara et al. | 215/364 |
| 4,639,242 | 1/1987 | Babson | 494/37 |
| 4,854,182 | 8/1989 | Ryan et al. | 422/102 X |
| 4,933,291 | 6/1990 | Daiss et al. | 422/72 X |
| 5,084,063 | 1/1992 | Korthoff | 606/226 |
| 5,084,240 | 1/1992 | Babson | 422/72 |
| 5,098,845 | 3/1992 | Babson | 436/415 |

*Primary Examiner*—James C. Housel
*Assistant Examiner*—Arlen Soderquist
*Attorney, Agent, or Firm*—Whitham & Marhoefer

[57] ABSTRACT

A centrifuge vessel for performing immunoassays, affinity chromatography, and like experiments includes a center tube and an outer waste chamber. A biomaterial is held within the center tube and is capable of binding specific analytes in test samples. In operation the centrifuge vessel is rotated at high speed about its longitudinal axis, thereby causing all fluid within the center tube to be transported into the outer waste chamber while the analyte of interest remains bound to the biomaterial positioned within the center tube In the centrifuge vessel, a cap connected to the outer waste chamber and extending over the center tube includes structure for preventing waste fluid expelled to the waste chamber from re-entering the center tube. In a first embodiment, the cap is either constructed from or the inside surface is coated with a hydrophobic material which repels fluids back into the waste chamber. In a second embodiment, the cap includes a dam which allows fluid to pass into the waste chamber but blocks the migration of waste fluid back to the center tube. In a third embodiment, the cap includes a sponge that allows fluids in the center tube influenced by the intense centrifugal forces generated during high speed rotation to pass into the waste chamber, but which prevents fluids in the waste chamber, which are influenced by relatively weaker forces, from returning to the center tube.

2 Claims, 2 Drawing Sheets

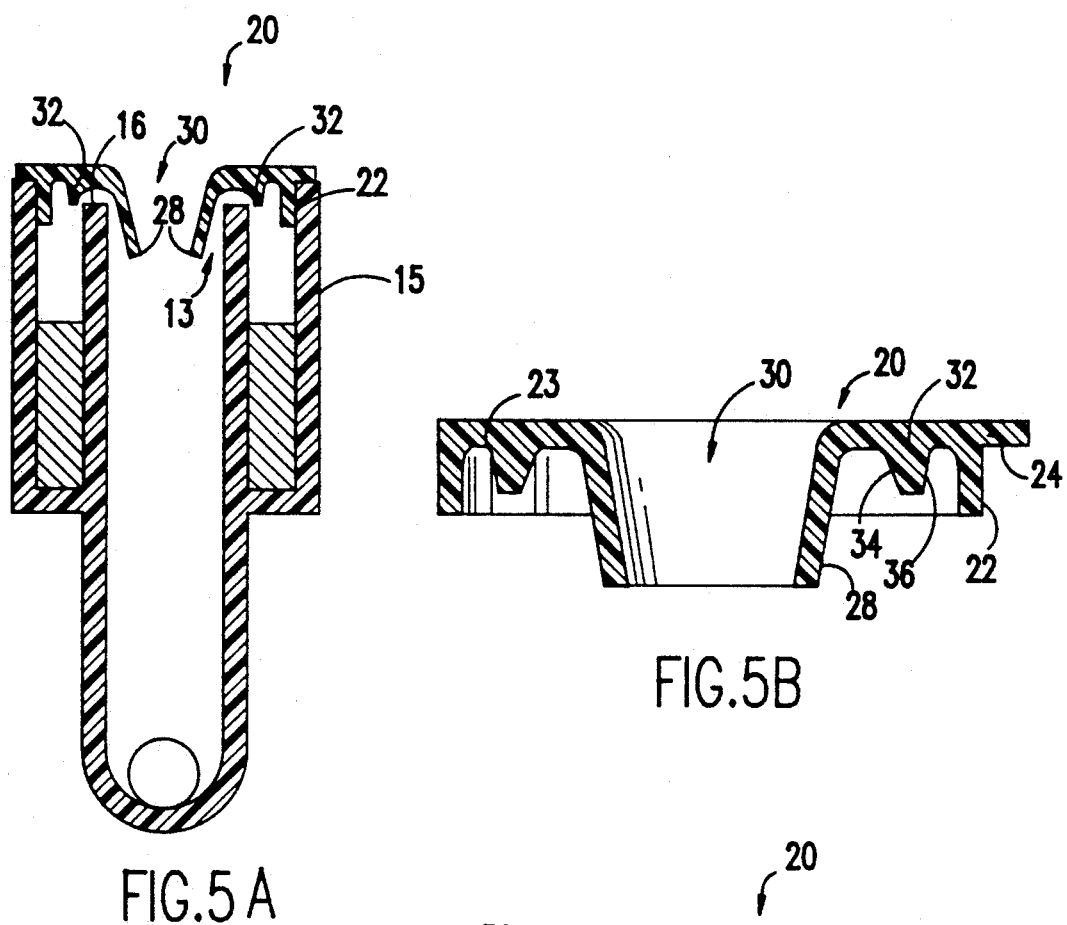
FIG.5A
FIG.5B
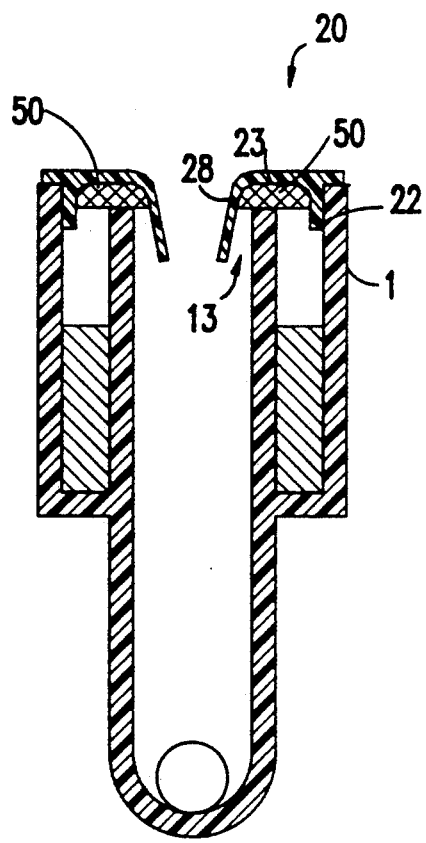
FIG.6

CENTRIFUGE VESSEL WITH COAXIAL WASTE CHAMBER HAVING CAP TO PREVENT WASTE FLUID TRANSFER FROM THE CHAMBER INTO THE VESSEL

BACKGROUND OF THE INVENTION

1. Field of the Invention

This invention generally relates to an improvement in a centrifuge vessel that is rotated at high speed about its longitudinal axis to separate an analyte from a biological solution in an automated fashion as is best described in U.S. Pat. No. 5,084,240 and U.S. Pat. No. 5,098,845. More particularly, the invention is directed to improvements which aid in retaining waste biological and wash fluid expelled from a central tube into an external waste chamber within the external waste chamber.

2. Description of the Prior Art

Centrifuges are well known commercial and laboratory tools that are used to separate materials of varying densities. Centrifuges are often used for clarifying liquids whereby suspended solids such as cells or proteins are sedimented from solution by high speed rotation of the centrifuge vessel. Two common types of centrifuges are the horizontal centrifuge and the fixed angle centrifuge.

In the conventional horizontal centrifuge, sample containers of the solution to be centrifuged are placed in holders called "buckets". These buckets are subsequently attached to a vertical rotor in a balanced arrangement and swung to a horizontal plane under centrifugal force. While being rotated at high speeds in the horizontal position, more dense particles in the sample move along an unimpeded path toward the bottom of the buckets to form a smooth, even "pellet" of sedimented material. The non-pelleted supernatant solution can be decanted from the bucket once centrifugation is halted.

In the conventional fixed angle centrifuge, a rotor holds a plurality of sample containers at fixed angles relative to the axis of rotation. In the same fashion as in the horizontal centrifuge, at least a pair of sample containers must be used in order to balance the rotor during high speed spinning. During high speed rotation of the fixed angle rotor, the denser particles in the sample containers pellet along the side wall of the container. Pelleting on the side wall does make decanting of the supernatant more difficult because of the possible resuspension of the pellet; however, there are certain advantages in using the fixed angle centrifuge. For example, in the fixed angle centrifuge there is a shorter path for sedimentation resulting in a shorter time for separation and, more importantly, higher speeds of rotation are achievable with fixed angle rotors because they are subjected to less air turbulence than the hanging bucket centrifuges. Higher rotation speeds allow greater centrifugal forces to act on the suspended solids.

In both the horizontal and the fixed angle centrifuges, the rotor must be balanced accurately in order to prevent damage to the centrifuge. In order to properly balance the rotor, the lab technician must precisely weigh each centrifuge sample container using a balance and then position two sample containers of equal weight in the rotor on opposite sides. This balancing step is very tedious and often requires withdrawing and adding back sample to the sample container until it reaches the desired weight.

In U.S. Pat. No. 4,639,242 to Babson, a vessel is described which allows for the complete physical separation of a precipitate and supernatant in a single tube. In operation, a precipitating agent is first mixed with the biological specimen and given time to react with analyte therein. Then the tube is rotated about its longitudinal axis at high speed. During high speed rotation, the contents of the tube is forced against the inner wall of the tube and moves upward towards the top of the tube due to the tube's inclined inner surface. At the top of the tube, the precipitate is deposited within V-shaped grooves on the tube's interior. After rotation is stopped, the precipitate is retained in the V-shaped grooves at the top of the tube while the liquid drops back to the bottom of the tube.

U.S. Pat. No. 4,639,242 to Babson also discloses a procedure for using the tube whereby a radioactively labelled antibody is bound in the bottom of the tube. The radioactively labelled antibody reacts with an analyte of interest in the biological fluid during a short incubation time during which the biological fluid is permitted to mingle with the bound antibody so that it may bind the analyte of interest. Then the tube is rotated at high speed, thereby causing the fluid in the tube to rise to the top while the analyte remains bound to the antibody in the bottom of the tube. The radioactivity in the bottom of the tube is counted while the tube is spinning.

While the tube disclosed in U.S. Pat. No. 4,639,242 to Babson is more adaptable to an automated processing environment than conventional horizontal and fixed angle centrifuges because it does not require the batch step of balancing pairs of rotor tubes, the Babson tube is not suitable for some of today's processing environments. For example, in some environments it may not be desirable to have a precipitation step. Not only does precipitation require extra chemicals to be used and time for the precipitation reaction to take place, but in some environments precipitation may reduce yield or the precipitating agent itself may affect the measured results. In addition, it may be desirable to stop the tube from spinning and use other instrumentation to make radioactive, fluorescent, or other related readings.

SUMMARY OF THE INVENTION

It is therefore an object of this invention to provide an improved centrifuge tube which includes a means for collecting biological fluid and wash liquid during rotation about its longitudinal axis and for storing that biological fluid and wash liquid separate from a bound analyte after the rotation of the centrifuge tube has ceased.

It is another object of this invention to provide a centrifuge tube which, upon rotation about its longitudinal axis, collects and holds biological and wash fluid in an attached waste chamber and prevents the transfer of the fluids back into the central tube portion of the centrifuge tube.

According to the invention, a centrifuge tube has been developed which is suitable for performing automated solid phase immunoassays. As a general rule, immunoassays in the clinical laboratory have rapidly replaced other methods used to detect or quantitate substances in body fluids with important biologic or pharmacologic properties. The high levels of sensitivity and specificity achieved with immunoassays result from the specific, high-affinity reversible binding of antigens to antibodies, and from the development of methods for attaching readily detected labels (radioactive isotopes, fluorescent or chemiluminescent molecules, enzymes and the like) to antigens or antibodies. Although radioactive isotopes have been the most extensively used label, they are not preferred because of concerns with radioactivity. Because of these concerns, the number of sensitive, specific immunoassays employing non-radioactive labels is rapidly expanding.

Many immunoassay procedures are based upon the reaction of either an antigen or antibody of interest (e.g., the "analyte") with a corresponding antibody or antigen which has been adsorbed or otherwise bound to a solid surface. These solid surfaces (hence the designation "solid-phase immunoassays") may be the interior of small test tubes (such as those available from Micromedic Systems, Inc. of Horsham, PA), microtiter trays (such as the 96 well trays available from Amersham International of Bucks, England), macrobeads (such as those available from Abbott Laboratories of Abbott Park, Illinois), or microparticles (such as those available from Pandex Laboratories, Inc. of Mundolein, Illinois), or magnetic particles (such as those available from Corning Medical of Medfield, MA). An advantage of solid-phase immunoassay over liquid-phase immunoassay is that common reagents and serum constituents which can potentially interfere with the measurement of the label are removed during the washing step of the solid-phase immunoassay procedure.

Immunoassays can be generally classified as competitive or noncompetitive. For exemplary purposes only, competitive and noncompetitive immunoassays are discussed below where an antibody is bound to the solid-phase; however, it should be understood that an antigen may also be used in like manner to the bound antibody.

Competitive immunoassays are generally used for small molecular weight analytes with only a single antibody binding site. In competitive immunoassays, the antigen present in the sample or standard competes with a measured amount of labeled antigen for a limited number of binding sites on a solid-phase bound antibody. After removal of any unreacted antigen from the test system, and washing of the solid support material, the bound label is quantitated by suitable means well known in the art (e.g., fluorescence, radioactivity, chemiluminescence, etc.). The amount of labeled antigen bound to the solid-phase antibody is inversely related to the concentration of antigen (analyte) in the sample or standard.

In noncompetitive immunoassays, the bound antibody binds all of the antigen in the sample at a first site, and a second, labelled antibody binds to a second site on all the bound antigen. Excess labelled antibody is then removed and the bound, labelled antibody is then quantitatively determined as a measure of bound antigen. These two separate antigen-antibody reactions can be conducted either sequentially with an intermediate washing step or simultaneously. This type of immunoassay is sometimes referred to as a "sandwich assay" because the antigen is sandwiched between the solid-phase and labeled antibodies. In addition, it is often referred to as an "immunometric assay" because the amount of label bound is usually a direct and linear function of the antigen concentration within the sample. If the labeled and solid-phase antibodies are directed to distinct antigenic determinants on the analyte, the assay may be referred to as a "two-site immunoassay". This type of assay can only be used with large molecular weight analytes with multiple antibody binding sites.

In an alternative sandwich assay format, the second antibody is unlabeled and the procedure is expanded to include an incubation of the sample with an excess of labeled third antibody specific for the IgG of the animal species from which the second antibody is elicited. In this instance, the immobilized and second antibodies are obtained from different animal species, in order to prevent the binding of labeled third antibody directly to the immobilized antibody. An advantage of this approach is that a single labeled antibody can serve as a common reagent for a number of analytes.

Common to all solid-phase immunoassays is the requirement that all unbound labeled antigen or antibody must be removed by thorough washing of the solid-phase prior to measurement of the label. Washing is a cumbersome procedure, particularly for automated analytical systems. For example, washing coated tubes or microwells by alternately adding and aspirating water or wash solution, as is customarily done, is inefficient since there is likely to be some residual solution in the tube or well after each wash cycle. As many as four to six washes of about 4 ml are required to adequately wash the coated tubes conventionally used in present day immunoassay procedures. Furthermore, provisions should be made to collect all the used wash fluid because it may contain infectious agents from the sample specimens.

The centrifuge vessel according to the present invention offers a number of advantages over the present protocols and apparatus conventionally used in solid-phase immunoassay procedures. As is generally shown in recently issued U.S. Pat. Nos. 5,084,240 and 5,098,845, the centrifuge vessel includes a central tube member and a peripheral waste chamber. In operation, the analyte being tested for reacts with and is bound to a solid support positioned in the central tube and the excess sample fluid, reagents, and wash fluid are separated from the bound analyte by rotating the tube rapidly about its longitudinal axis. High speed rotation causes the fluids to move up the inclined wall of the central tube and drop into the peripheral waste chamber. Rotation continues until no fluid residue remains in the bottom of the tube. After rotation of the tube is halted, the excess sample fluid, reagents and wash fluid are safely stored in the waste chamber and do not re-mix with the bound analyte in the central tube.

A particular advantage of the centrifuge tube design is that multiple washings of the bound analyte can be performed in a sequential fashion as rapidly as the wash solution can be pipetted into the central tube of the vessel. The ability to wash the bound analyte in the rapid fashion results from the excess fluids being transferred to the waste chamber almost instantaneously because of the high speed centrifugal forces acting on the centrifuge vessel. Because of the speed with which washing is accomplished, multiple vessels may be processed sequentially without impairing sample throughput. The speed of processing the vessels allows for the precise control of the incubation times required by immunoassays, and allows for the normally labor-intensive immunoassay procedure to be automated.

This invention particularly solves a problem encountered with the centrifuge vessel discussed in U.S. Pat. Nos. 5,084,240 and 5,098,845. Specifically, it has been found that waste biological and wash fluid has a tendency to either splash up or climb up the outside wall of the waste chamber during high speed rotation of the centrifuge tube and migrate across the cap towards the center of the centrifuge vessel to a point above the central tube. After rotation of the centrifuge tube ceases, a droplet of waste biological or wash fluid which includes free antibody or antigen may hang from the cap above the central tube which contains the bound antibody or antigen. If the droplet falls into the central tube, inaccuracies will result since free antigen or antibody will be combined with bound antigen or antibody. Therefore, this invention provides centrifuge tube devices like those in U.S. Pat. Nos. 5,084,240 and 5,098,845 with features specifically designed to prevent the migration of waste fluid in the waste chamber back into the central tube portion of the centrifuge tube.

In a first embodiment of the invention, the cap which fits over the top portion of the centrifuge vessel is made from a hydrophobic plastic material (e.g., one which contains a wax or silicone compound or the like). The hydrophobic nature of the cap will repel fluid back into the waste chamber and prevent it from being transported to a point above the central tube. Alternatively, the inside portion of the cap could be coated with a hydrophobic material such as wax, silicone or polytetrafluorethylene.

In a second embodiment of the invention, the cap which fits over the top portion of the centrifuge vessel includes a dam which partially extends into the waste chamber. The inner wall of the dam is tapered away from the central tube. Fluid exiting the central tube during the high speed rotation step contacts the tapered inner wall of the dam and is guided into the waste chamber. However, fluid present in the waste chamber is prevented from migrating to a point above the central tube by the outer wall of the dam. In addition, the spacing between the inner wall of the dam and the top of central tube is constricted (e.g., on the order of 10-20 mls (thousandths of an inch)). Conversely, the spacing between the top of the central tube and the flange portion of the cap which partially extends into the central tube is three to five times greater. Hence, the spacing between the dam and the center tube acts as a capillary which will, under the influence of the centrifugal forces produced during high speed rotation, allow waste fluid to be transported into the waste chamber, but will prevent waste fluid from travelling in the reverse direction.

In a third embodiment of the invention, the cap which fits over the top portion of the centrifuge vessel has a doughnut shaped sponge positioned thereon. The sponge allows fluid to pass from the central tube to the waste chamber under the influence of the high centrifugal forces generated during the rotation step, but prevents fluid in the waste chamber from re-entering the central tube.

BRIEF DESCRIPTION OF THE DRAWINGS

The various aspects, advantages, and principles of the present invention, and the preferred embodiments thereof, will be best understood by reference to the accompanying drawings in which:

FIGS. 5A-B are a cross-sectional side views of a cap construction having a dam positioned on and off a centrifuge vessel, respectively; and FIG. 6 is a cross-sectional side view of a cap construction having a sponge positioned on a centrifuge vessel.

DETAILED DESCRIPTION OF THE PREFERRED EMBODIMENTS OF THE INVENTION

Figure 1:
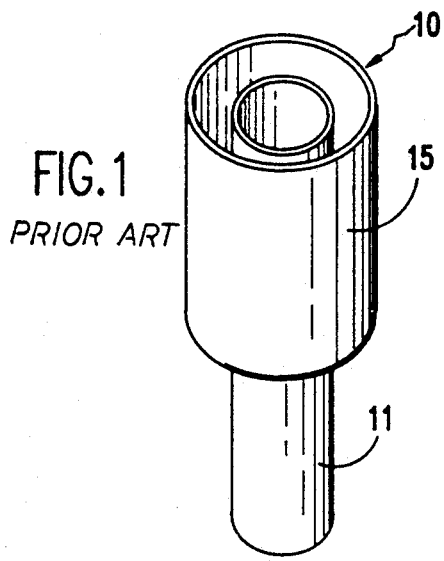
FIG. 1 is an isometric view of a centrifuge vessel.
Figure 2:
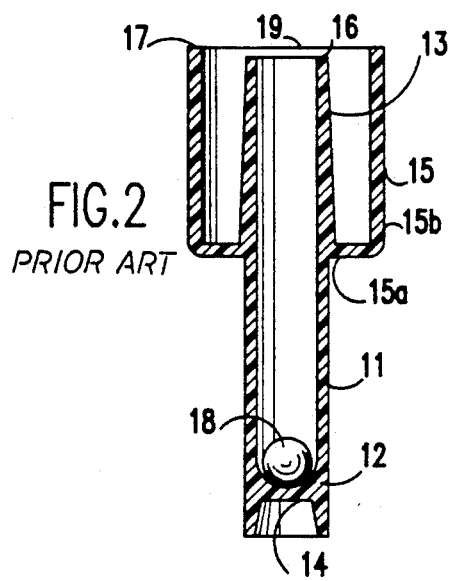
FIG. 2 is a cross-sectional side view of the centrifuge vessel of FIG. 1.

Referring now to the drawings and, more particularly to FIGS. 1 and 2, which show the centrifuge vessel 10 according to the present invention comprises a longitudinally extending central tube 11 opened at the top 16 of its upper end portion 13, and closed at its lower end portion 12. Integrally attached to tube 11 at a point between the upper and lower ends is a generally cylindrical waste chamber 15 having a circumferentially extending bottom portion 15a extending between tube 11 and the waste chamber's upwardly extending cylindrical side wall 15b. The waste chamber 15 is open at its uppermost end 17 at a point above the top 16 of the tube 11. The waste chamber is coaxial with the tube 11, and has an inner diameter greater than the outer diameter of the tube 11.

Although the centrifuge vessel 10 may be manufactured from various materials, for ease of manufacture it is preferred that the vessel be molded from a plastic (polymeric) material which is compatible with its intended use. Polyethylene, polypropylene, and other materials are suitable for use in the centrifuge vessel construction.

The lower end 12 of the vessel 10 may be formed with a drive socket 14 which is engaged by a rotatable axle member for rotating the vessel 10 about its longitudinal axis. However, other means for rotating vessel 10 about its longitudinal may be employed such as by employing drive wheels to engage the outside wall of either the waste chamber 15 or lower portion of tube 11. In which case, a drive socket 15 need not be required (see FIG. 5a).

As is explained in U.S. Pat. Nos. 5,084,240 and 5,098,845, when the vessel 10 is rotated at high speed about its longitudinal axis, fluid within the central tube 11 travels upward along the inner surface of the tube 11. The inner surface of the tube 1 is preferably manufactured so that the closed bottom 12 of the tube 11 has a slightly smaller inner diameter than the open top 16, whereby the outward flaring of the inner surface of the tube 11 provides an incline which aids in transporting fluid upward. The uppermost terminal end 16 of tube 11 is below of the cross-sectional plane passing through and defining the open uppermost end 17 of the waste chamber 15. This difference in height provides a passage which allows fluid to pass from tube 11 into waste chamber 15.

As explained in U.S. Pat. No. 5,084,240, the waste chamber 15 may be manufactured with its inner diameter at the bottom portion 15a slightly greater than its inner diameter at its uppermost end 17 to aid in holding fluid at a position towards the base of waste chamber 15 during rotation of the centrifuge vessel 10. The centrifuge vessel 10 does not need to be removed from the drive means to discard biological or wash fluid between washings since all of the wash fluid is transported to and held in waste chamber 15. Therefore, multiple washings are performed simply by repetitively pipetting wash fluid into the vessel 10 and discarding the waste wash fluid by rotating the centrifuge vessel 10 about its longitudinal axis at high speed.

The bottom inner portion of the tube 11 may be coated with an antigen or antibody protein which binds to the inner surface of the tube 11. This coating preferably extends from the very bottom of the closed end 12 of the tube 11 upwards to a point anywhere less than about 25% of the overall length of tube 11 where the actual length of the coating is a matter of design of the coating process for manufacture of the coated tube. As an alternative to coating the inner surface of the tube 11 with a specific antigen or antibody, or as a means for providing for additional reaction surfaces for the desired immunoassay procedure, a solid support 18 can be placed within the tube 11 where the solid support includes a binding surface, such as a bound antigen or antibody molecule, for selectively binding a specific analyte in the biological fluid under test. Suitable solid supports 18 may include antigen or antibody coated spheres of organic polymers or inorganic polymers. Silica gels are a typical example of inorganic polymers used as binding spheres. In U.S. Pat. No. 5,084,240, a macro bead solid support is utilized and in the co-pending U.S. Pat. application Ser. No. 07/796,540, which is herein incorporated by reference, microbeads are used as the solid support.

Figure 3:
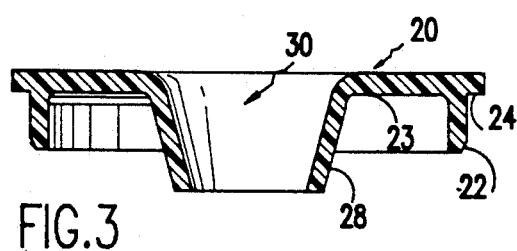
FIG. 3 is a cross-sectional side view of a cap which fits on the centrifuge vessel of FIG. 2.
Figure 4:
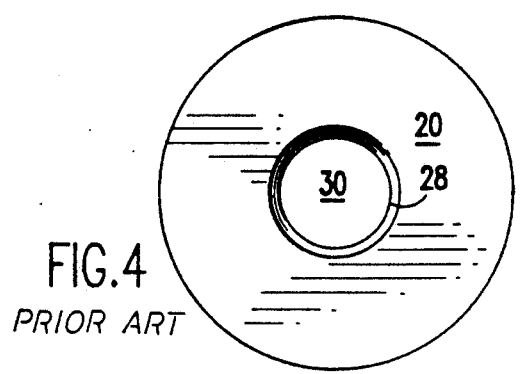
FIG. 4 is a top view of the cap of FIG. 3.

FIGS. 3 and 4 show a hard cover cap 20 similar to that shown and described in U.S. Pat. No. 5,084,240. The cap 20 has an outer flange 22 which fits inside and adjacent the inner diameter of sidewall 15b of waste chamber 15. An opening 30 in the central portion of the cap 20 allows free access to the central tube 11 of the centrifuge vessel 10 and all pipetting of biological sample and wash fluid into the centrifuge vessel 10 is performed through this opening 30. A plastic film (not shown) can be provided over the opening 30 to protect the bound biomaterial at the base of tube 11 during storage prior to conducting an immunoassay. While the cap 20 may be connected to the centrifuge vessel 10 by a tight frictional fit between the flange 22 and the waste chamber 15, ideally the extended portion 24 of the cap 20 is welded or glued to the top 17 of the waste chamber. Welding or gluing the cap 20 to the waste chamber 15 provides for a more secure fit and allows for pressure testing the centrifuge vessel 10 prior to sale for enhanced quality assurance.

The cap 20 includes an inner flange 28 that projects down into the top portion 13 of the center tube 11. The diameter of the inner flange 28 is smaller than the diameter of the top portion 13 of the center tube 11 so that fluid can pass over the top 16 of the center tube 11 and into the waste chamber 15. The inner flange 28 helps prevent waste biological and wash fluid from splashing out of the centrifuge vessel during high speed rotation. In addition, for macrobead based immunoassay tubes, the inner flange 28 helps prevent the macrobead with the bound biomaterial 18 from being transferred into the waste chamber (e.g., the macrobead 18 is sized larger than the distance between the downward projecting inner flange 28 of the cap 20 and the top 16 of the center tube 11.

It is envisioned that the centrifuge vessel 10 will be sold as a single-use, disposable, immunoassay test device where a biomaterial 18 designed for testing for a particular constituent in urine, blood, or other fluid will be placed in the center tube 11, and the cap 20 will be attached securely to the waste chamber 15 prior to shipping.

While the centrifuge vessel 10 design of U.S. Pat. Nos. 5,084,063 and 5,098,845 has many advantages in performing automated immunoassays, it has been discovered that there is a tendency for some portion of waste biological and wash fluid which has been deposited in the waste chamber 15 to travel up the inside of side wall 15b, across the inside top surface 23 of cap 20, down the flange 28 of cap 20, and back into the center tube 11. Sometimes a portion of the waste biological fluid or wash fluid collects as a droplet on the end of inner flange 28 and there is a tendency for this droplet to fall into the central tube 11 when the centrifuge vessel 10 is transferred to a fluorimeter, luminometer, scintillation counter or other measurement device. Because of the presence of free, unbound antigen or antibody in the waste fluids, having a droplet of the waste fluid fall into the central tube 11 seriously affects the measurement accuracy for the immunoassay. It is not clear how or why some of the waste fluids from the waste chamber 15 move towards the center tube 11 on the top inside surface 23 of cap 20, but it may be caused by splashing during high speed rotation of centrifuge vessel 10, capillary action between the flange 28 and top 16 of center tube 11, or by some other means. It is noted that because the waste chamber 15 is attached to the center tube 11, the centrifugal forces resulting from high speed rotation of the centrifuge vessel 10 about its longitudinal axis which act on fluid within the center tube 11 also act on the fluid within the waste chamber 15. This invention particularly addresses the problem of movement of waste fluid from the waste chamber 15 back into the center tube 11.

In a first embodiment of the invention, the cap 20 shown in FIGS. 3 and 4 is made of a hydrophobic material or, alternatively, is coated with a hydrophobic material. When the top inside portion 23 of the cap 20 is hydrophobic, waste fluid which is splashed or migrates up to the inside portion 23 of the cap 20 will be repelled and will drop back into the waste chamber 15. A suitable hydrophobic cap 20 can be prepared by blending the polymeric cap forming material (e.g., polyethylene, polypropylene, etc.) with 2% wax, silicone, polytetrafluoroethylene, or some other suitable hydrophobic substance. In addition, wax, silicone, polytetrafluoroethylene, or other suitable hydrophobic substances may be applied to the inside 23 surface of cap 20 by spraying, dipping, painting, or some other suitable operation.

FIGS. 5A-B illustrate a second embodiment of the invention where cap 20 includes a dam 32 that projects down into the waste chamber 15 to a point below the upper portion 13 of the central tube 11. The dam 32 has a radius which is greater than that of the inner flange 28 and less than that of the outer flange 22. Waste fluid exiting the central tube 11 contacts a tapered inner wall 34 of the dam 32 and is directed into the waste chamber 15. Fluid which is transported back to the top of the waste chamber 15 and the inside top surface 23 of cap 20 by capillary action, splashing, centrifugal forces or the like, is redirected by an outer dam wall 36 back into the waste chamber 15. Hence, the dam 32 performs a similar function to the use of a hydrophobic material for constructing the cap in that it blocks waste fluid from re-entering the central tube 11. The features of the first and second embodiment might advantageously be combined, wherein a cap 20 would include both a dam 32 and be coated with a hydrophobic material.

Another important mode of operation of the dam 32 relates to the formation of a constricted capillary passage between the top 16 of the center tube 11 and the inner wall 34 of the dam 32. The spacing between the top 16 of the center tube 11 and the inner wall 34 is advantageously on the order of 10-20 mls, while the spacing between the top 16 of the center tube 11 and the flange 28 of the cap 20 is three to five times larger. The narrow passage created between the top 16 of center tube 11 and the inner wall of the dam 34 is positioned over the waste chamber 15 so that fluid in the passage will fall in the waste chamber 15. Because the passage is constricted, the centrifugal forces generated during high speed rotation of the centrifuge vessel 10 force waste fluid from the central tube 11 through the passage and into the waste chamber 15. However, fluids from the waste chamber 15 are not permitted to pass back through the passage since no forces are present to cause such a reverse migration through the passage.

FIG. 6 illustrates a third embodiment of the invention where the cap 20 includes an annular sponge 50 positioned between the top portion 13 of the center tube 11 and inside surface 23 of the cap 20. Although not a requirement, preferably the sponge 50 is flush with the inside surface 23 of cap 20 and the top 16 of the center tube 11, and has an outer radius 52 which contacts flange 22 and an inner radius 54 which contacts the flange 28. The sponge could be made of an open celled plastic material of the type which is commonly used to make air filters. The characteristics of the sponge 50 will be such that fluids acted on by the intense centrifugal forces generated when the centrifuge vessel 10 rotates about its longitudinal axis at high speeds pass from the center tube 11 to the waste chamber 15; however, fluids in the waste chamber 15 which might be acted on by relatively small forces, such as capillary action or splashing, are prevented by the sponge 50 from re-entering the central tube 11.

While the centrifuge vessel 10 has been discussed exclusively in conjunction with immunoassays, other procedures, such as affinity chromatography, may be conducted with the centrifuge vessel 10.

While the invention has been described in terms of its preferred embodiments, those skilled in the art will recognize that the invention may be practiced with modification within the spirit and scope of the appended.

Having thus described out invention, what we intend to claim and secure by Letters Patent is the following:

1. A centrifuge vessel, comprising:
    a tube rotatable about a longitudinal axis through said tube;
    a biomaterial positioned within said tube;
    a waste chamber connected to said tube and positioned to catch and hold fluids expelled from out a top opening of said tube; and
    a cap connected to said waste chamber and extending over said tube, said cap having an opening allowing access to said tube and a flange positioned at said opening which extends to a point below said top opening of said tube, said flange being spaced from said top opening of said tube to allow fluid to pass from said tube to said waste chamber, said cap including a dam projecting from said cap which is positioned outside and encircles said top opening of said tube and projects to a point below said top opening of said tube.

2. A centrifuge vessel as recited in claim 1 wherein a first distance between said flange of said gap and said top of said tube is three to five times greater than a second distance between said top of said tube and said dam of said cap.

* * * * *

UNITED STATES PATENT AND TRADEMARK OFFICE
CERTIFICATE OF CORRECTION

PATENT NO. : 5,244,635
DATED : September 14, 1993
INVENTOR(S) : Babson et al.

It is certified that error appears in the above—identified patent and that said Letters Patent is hereby corrected as shown below:

On title page, item [19] change

"Rabson et al." to -- Babson et al. ---

On title page, item [75], change "Rabson"

to -- Babson ---

Signed and Sealed this

Twenty-second Day of March, 1994

Attest:

BRUCE LEHMAN

*Attesting Officer*       *Commissioner of Patents and Trademarks*